US009056068B2

(12) United States Patent
Nutman et al.

(10) Patent No.: US 9,056,068 B2
(45) Date of Patent: Jun. 16, 2015

(54) **VACCINE AND METHODS OF USE AGAINST *STRONGYLOIDE STERCORALIS* INFECTION**

(75) Inventors: Thomas B. Nutman, Chevy Chase, MD (US); David Abraham, Wynnewood, PA (US)

(73) Assignees: The United States of America, as represented by the Secretary, Department of Health and Human Services, Washington, DC (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 13/575,987

(22) PCT Filed: Feb. 1, 2011

(86) PCT No.: PCT/US2011/023320
§ 371 (c)(1),
(2), (4) Date: Aug. 15, 2012

(87) PCT Pub. No.: WO2011/097216
PCT Pub. Date: Aug. 11, 2011

(65) Prior Publication Data
US 2012/0308599 A1    Dec. 6, 2012

Related U.S. Application Data

(60) Provisional application No. 61/301,426, filed on Feb. 4, 2010.

(51) Int. Cl.
*A61K 39/02*  (2006.01)
*A61K 39/00*  (2006.01)
*C07K 14/435* (2006.01)

(52) U.S. Cl.
CPC ......... *A61K 39/0003* (2013.01); *C07K 14/4354* (2013.01)

(58) Field of Classification Search
None
See application file for complete search history.

(56) References Cited

U.S. PATENT DOCUMENTS

| | | | |
|---|---|---|---|
| 5,225,539 | A | 7/1993 | Winter |
| 5,449,752 | A | 9/1995 | Fujii et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobovits |
| 6,265,150 | B1 | 7/2001 | Terstappen et al. |
| 2002/0197266 | A1 | 12/2002 | Debinski |

FOREIGN PATENT DOCUMENTS

| | | |
|---|---|---|
| EP | 0 239 400 B1 | 8/1994 |
| GB | 2 188 638 A | 10/1987 |

OTHER PUBLICATIONS

De'Broski et al (Experimental Parasitology. 2002. 100: 112-120).*
Abraham et al., "Immunization with the recombinant antigen Ss-IR induces protective immunity to infection with *Strongyloides stercoralis* in mice," *Vaccine*, 29 (45), 8134-8140 (2011).
Brigandi et al., "*Strongyloides stercoralis:* Role of Antibody and Complement in Immunity to the Third Stage Larvae in BALB/cBYJ Mice," *Exp. Parasitol.*, 82 (3), 279-289 (1996).
Brindley et al., "Antigens from the surface and excretions/secretions of the filariform larva of *Strongyloides stercoralis*," *Mol. Biochem. Parasitology*, 28 (3), 171-180 (1988).
Conder et al., "Immunization with infective larvae of *Strongyloides ratti* (Nematoda) exposed to microwave radiation," *J. Parasit.*, 69 (1), 83-87 (1983).
EBI Accession No. UniProt:O44394 (Jun. 1, 1998).
Gallego et al., "Identification of an astacin-like metallo-proteinase transcript from the infective larvae of *Strongyloides stercoralis*," *Parasitol Int.*, 54 (2), 123-133 (2005).
Haskard et al., "The Production of Human Monoclonal Autoantibodies from Patients with Rheumatoid Arthritis by the EBV-Hybridoma Technique," *J. Immunol. Methods.*, 74 (2), 361-367 (1984).
Herbert et al., "Immunoaffinity-isolated antigens induce protective immunity against larval *Strongyloides stercoralis* in mice," *Exp. Parasitology*, 100 (2), 112-120 (2002).
Hudecz et al., "Synthesis of Peptide Bioconjugates," *Methods Mol. Biol.*, 298 (Ch. 13), 209-223 (2005).
Huse et al., "Generation of a Large Combinatorial Library of the Immunoglobulin Repertoire in Phage Lambda," *Science*, 246, 1275-1281 (1989).
International Search Report, Application No. PCT/US2011/023320, dated Apr. 28, 2011.
Keiser et al., "*Strongyloides stercoralis* in the Immunocompromised Population," *Clin. Microbiol. Rev.*, 17 (1), 208-217 (2004).
Kerepesi et al., "DNA Immunization with $Na^+$-$K^+$ ATPase (*Sseat-6*) Induces Protective Immunity to Larval *Strongyloides stercoralis* in Mice," *Infect. Immunity*, 73 (4), 2298-2305 (2005).
Kerepesi et al., "Human Immunoglobulin G Mediates Protective Immunity and Identifies Protective Antigens against Larval *Strongyloides stercoralis* in Mice," *J. Infect. Dis.*, 189 (7), 1282-1290 (2004).
Kirin et al., "Amino Acid and Peptide Bioconjugates of Copper(II) and Zinc(II) Complexes with a Modified *N,N*-Bis(2-picolyl)amine Ligand," *Inorg. Chem.*, 44 (15), 5405-5415 (2005).

(Continued)

*Primary Examiner* — Jennifer Graser
(74) *Attorney, Agent, or Firm* — Leydig, Voit & Mayer, Ltd.

(57) ABSTRACT

The polynucleotide encoding the SSIR gene from the nematode *Strongyloides stercoralis* is provided, along with the polypeptide encoded by the SSIR gene. It was found that when mice were immunized with the SSIR polypeptide vaccine, it provided immunity to mice which were implanted with *Strongyloides stercoralis* L3 implants. Methods for making the SSIR protein, recombinant vectors encoding the SSIR gene, a vaccine made from the SSIR protein, and methods of use are also provided.

14 Claims, 6 Drawing Sheets

(56) References Cited

OTHER PUBLICATIONS

Köhler et al., "Derivation of specific antibody-producing tissue culture and tumor lines by cell fusion," *Eur. J. Immunol.*, 6, 511-519 (1976).

Krolewiecki et al., "Improved Diagnosis of *Strongyloides stercoralis* Using Recombinant Antigen-Based Serologies in a Community-Wide Study in Northern Argentina," *Clin. Vaccine Immunol.*, 17 (10), 1624-1630 (2010).

Mejia et al., "Screening, prevention, and treatment for hyperinfection syndrome and disseminated infections caused by *Strongyloides stercoralis*," *Curr. Opin. Infect. Dis.*, 25 (4), 458-463 (2012).

Mitreva et al., "Comparative Genomics of Gene Expression in the Parasitic and Free-Living Nematodes *Strongyloides stercoralis* and *Caenorhabditis elegans*," *Genome Res.*, 14 (2), 209-220 (2004).

Northern et al., "*Strongyloides stercoralis*: Antigenic analysis of infective larvae and adult worms," *Int'l J. Parasitology*, 20 (3), 381-387 (1990).

Pedersen et al., "Comparison of Surface Accessible Residues in Human and Murine Immunoglobulin Fv Domains," *J. Mol. Biol.*, 235, 959-973 (1994).

Ramanathan et al., "A luciferase immunoprecipitation systems assays enhances the sensitivity and specificity of diagnosis of *Strongyloides stercoralis* infection," *J. Infect. Diseases*, 198 (3), 444-451 (2008).

Ramanathan et al., "*Strongyloides stercoralis* Infection in the immunocompromised host," *Curr. Infect. Dis. Rep.*, 10 (2), 105-110 (2008).

Ramanathan et al., "Microarray-Based Analysis of Differential Gene Expression between Infective and Noninfective Larvae of *Strongyloides stercoralis*," *PLos Negl. Trop. Dis.*, 5 (5), e1039 (2011).

Ravi et al., "Characterization of a recombinant immunodiagnostic antigen (NIE) from *Strongyloides stercoralis* L3-stage larvae," *Mol. Biochem. Parasitology*, 125 (1-2), 73-81 (2002).

Ravi et al., "*Strongyloides stercoralis* recombinant NIE antigen shares epitope with recombinant Ves v 5 and Pol a 5 allergens of insects," *Am. J. Trop. Med. Hyg.*, 72 (5), 549-553 (2005).

Roder et al., "The EBV-Hybridoma Technique," *Meth. Enzymol.*, 121, 140-167 (1986).

Wang et al., "Infection of mice with the helminth *Strongyloides stercoralis* suppresses pulmonary allergic responses to ovalbumin," *Clin. Experimental Allergy*, 31 (3), 495-500 (2001).

Abraham et al., "*Strongyloides stercoralis*: Protective Immunity to Third-Stage Larvae in BALB/cByJ Mice," *Experimental Parasitology*, 80(2), 297-307 (1995).

GenBank Accession: AAB97359.1, "IgG immunoreactive antigen [*Strongyloides stercoralis*]" (1998).

GenBank Accession: AAD46493.1, "L3NieAg.01 [*Strongyloides stercoralis*]" (2005).

\* cited by examiner

Figure 1A

AACAGCGCGCGTGTGGAAAATCAGGATCAAAAAGACCAGCTGGAAAACCAAGA
CCAGAAAGATCAGCTGGAAAATCAGGACCAGAAAAACCAGCTGAAAAATCAAA
GCGAAAACCAGGATCAGAAAAACCAACTGAAAAACCAGTCTGAAAATCAGGAT
CAGAAAAAACCGATCAAAAAACCTATCAAAAAACCGGGCCCGAAACCGATTCGC
CCGATCGTTAAACCGAAACCGAAAACCACGACCCAGGCACCGGAAGAACCGGA
AGGTCCGGAAGAACCGGAAGGCCCTGAGGAACCGGAAGGCCCGGAAGGCCCTG
AAGAGCCGGAAGGCCCGGCCGGCCCTGAAGAACCTGAAGGCCCGGCCGGCCCC
GAGGAGCCTGAGGGTCCTGAAGAACCGGAAGGCCCGGCTGGTCCGGAAGAACC
GCGTGATGACGATGACGGTGTGGATGAAGAAGACGAACGCAT (SEQ ID NO: 1)

Figure 1B

NSARVENQDQKDQLENQDQKDQLENQDQKNQLKNQSENQDQKNQLKNQSENQDQ
KKPIKKPIKKPGPKPIRPIVKPKPKTTTQAPEEPEGPEEPEGPEEPEGPEGPEEPEGPAGP
EEPEGPAGPEEPEGPEEPEGPAGPEEPRDDDDGVDEEDERD (SEQ ID NO: 2)

SEQUENCE LISTING

```
<160> NUMBER OF SEQ ID NOS: 5

<210> SEQ ID NO 1
<211> LENGTH: 467
<212> TYPE: DNA
<213> ORGANISM: Strongyloides stercoralis

<400> SEQUENCE: 1
aacagcgcgc gtgtggaaaa tcaggatcaa aaagaccagc tggaaaacca agaccagaaa      60
gatcagctgg aaaatcagga ccagaaaaac cagctgaaaa atcaaagcga aaaccaggat     120
cagaaaaacc aactgaaaaa ccagtctgaa atcaggatc agaaaaaacc gatcaaaaaa      180
cctatcaaaa aaccgggccc gaaaccgatt cgcccgatcg ttaaaccgaa accgaaaacc     240
acgacccagg caccggaaga accggaaggt ccggaagaac cggaaggccc tgaggaaccg     300
gaaggcccgg aaggccctga agagccggaa ggcccggccg gccctgaaga acctgaaggc     360
ccggccggcc ccgaggagcc tgagggtcct gaagaaccgg aaggcccggc tggtccggaa     420
gaaccgcgtg atgacgatga cggtgtggat gaagaagacg aacgcat                   467

<210> SEQ ID NO 2
<211> LENGTH: 156
<212> TYPE: PRT
<213> ORGANISM: Strongyloides stercoralis

<400> SEQUENCE: 2

Asn Ser Ala Arg Val Glu Asn Gln Asp Gln Lys Asp Gln Leu Glu Asn
1               5                   10                  15

Gln Asp Gln Lys Asp Gln Leu Glu Asn Gln Asp Gln Lys Asn Gln Leu
                20                  25                  30

Lys Asn Gln Ser Glu Asn Gln Asp Gln Lys Asn Gln Leu Lys Asn Gln
            35                  40                  45

Ser Glu Asn Gln Asp Gln Lys Lys Pro Ile Lys Lys Pro Ile Lys Lys
    50                  55                  60

Pro Gly Pro Lys Pro Ile Arg Pro Ile Val Lys Pro Lys Pro Lys Thr
65                  70                  75                  80

Thr Thr Gln Ala Pro Glu Glu Pro Glu Gly Pro Glu Glu Pro Glu Gly
                85                  90                  95

Pro Glu Glu Pro Glu Gly Pro Glu Gly Pro Glu Glu Pro Glu Gly Pro
                100                 105                 110

Ala Gly Pro Glu Glu Pro Glu Gly Pro Ala Gly Pro Glu Glu Pro Glu
            115                 120                 125

Gly Pro Glu Glu Pro Glu Gly Pro Ala Gly Pro Glu Glu Pro Arg Asp
        130                 135                 140

Asp Asp Asp Gly Val Asp Glu Glu Asp Glu Arg Asp
145                 150                 155
```

```
<210> SEQ ID NO 3
<211> LENGTH: 55
<212> TYPE: DNA
<213> ORGANISM: Artificial Sequence
<220> FEATURE:
<223> OTHER INFORMATION: Synthetic

<400> SEQUENCE: 3
cttctggccg ctgcagccca ttctgcattt gcgaactccg cccgcgtgga gaatc        55

<210> SEQ ID NO 4
<211> LENGTH: 56
<212> TYPE: DNA
<213> ORGANISM: Artificial Sequence
<220> FEATURE:
<223> OTHER INFORMATION: Synthetic

<400> SEQUENCE: 4
gcttctggcc gctgcagccc attctgcatt tgcgaactcc gcccgcgtgg agaatc       56

<210> SEQ ID NO 5
<211> LENGTH: 77
<212> TYPE: DNA
<213> ORGANISM: Artificial Sequence
<220> FEATURE:
<223> OTHER INFORMATION: Synthetic

<400> SEQUENCE: 5
ggggacaact ttgtacaaaa aagttggcac catggtaagc gctattgttc tgtacgtgct   60
tctggccgct gcagccc                                                 77
```

VACCINE AND METHODS OF USE AGAINST *STRONGYLOIDE STERCORALIS* INFECTION

CROSS-REFERENCE TO RELATED APPLICATION

This application is a U.S. National Phase of International Patent Application No. PCT/US11/23320, filed Feb. 1, 2011, which claims the benefit of U.S. Provisional Patent Application No. 61/301,426, filed Feb. 4, 2010, the entire contents of which are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,073 Byte ASCII (Text) file named "710729_ST25.TXT," dated Jul. 19, 2012.

BACKGROUND OF THE INVENTION

*Strongyloides stercoralis* is a nematode, estimated to infect 30-100 million people, humans, primates and dogs around the globe, and ordinarily causes a range of relatively benign symptoms during acute infection. Chronic *S. stercoralis* infections may persist for the lifetime of the host and are commonly subclinical. Chronically infected individuals however, who later become immunosuppressed, often because of corticosteroid treatment, or infection will HTLV-1, can disseminate *S. stercoralis*, a condition termed "hyperinfection," that can become life threatening. Although chemotherapy is available for acute and chronic infections, treatment of the potentially lethal hyperinfection syndrome remains problematic. Thus, given the potential for fatal disease associated with *S. stercoralis* infection and the difficulty in treatment of hyperinfection, there remains a need for new immunostimulatory compositions, vaccines and treatments against this infection.

BRIEF SUMMARY OF THE INVENTION

A protein termed *Strongyloides stercoralis* immunoreactive antigen (SSIR) has been discovered. The SSIR antigen is mixed with an adjuvant, and used to immunize mice. In experiments, the immunization protocol protected mice from challenge infection with *S. stercoralis*. Moreover, sera from protected mice when transferred to naive mice, protected these naive mice from challenge infection.

In an embodiment, the present invention provides an isolated antigen from *Strongyloides stercoralis* stage L3, comprising the *S. stercoralis* immunoreactive antigen (SSIR) protein.

In another embodiment, the invention provides a polynucleotide which encodes the SSIR antigen of *S. stercoralis* and is provided as SEQ ID NO: 1.

In an alternate embodiment the invention provides a polynucleotide which is complementary to the polynucleotide provided as SEQ ID NO: 1.

In another embodiment, the invention provides a SSIR polypeptide having the amino acid sequence of SEQ ID NO: 2, encoded by the polynucleotide of SEQ ID NO: 1.

In another embodiment, the invention provides a composition comprising the polynucleotide of SEQ ID NO: 1 or the polypeptide of SEQ ID NO: 2, and a pharmaceutically acceptable carrier. In yet another embodiment, the composition further comprise an adjuvant.

In an embodiment, the invention also provides a method of use of the polypeptide of SEQ ID NO: 2, to prepare a therapeutic composition or vaccine against *S. stercoralis*.

In a further embodiment, the invention provides a method of vaccinating a patient against *S. stercoralis* infection comprising introducing into the patient, a composition comprising the polypeptide of SEQ ID NO: 2, and a pharmaceutically acceptable carrier under conditions sufficient for said patient to develop a protective immune response.

In yet another embodiment, the invention provides a method of use of the SSIR antigen (SEQ ID NO: 2) encoded by the polynucleotide of SEQ ID NO: 1 for identifying analogous antigens in other parasitic nematodes.

In yet a further embodiment, the invention provides a method of use of the SSIR antigen (SEQ ID NO: 2) encoded by the polynucleotide of SEQ ID NO: 1 for identifying analogous antigens which can act as an immunosuppressant in patients with severe allergies.

BRIEF DESCRIPTION OF THE SEVERAL VIEWS OF THE DRAWING(S)

FIGS. 1A and 1B show the polynucleotide sequence of SSIR (SEQ ID NO: 1) from *S. stercoralis* and the polypeptide encoded by the polynucleotide (SEQ ID NO: 2).

DETAILED DESCRIPTION OF THE INVENTION

Figure 2A:
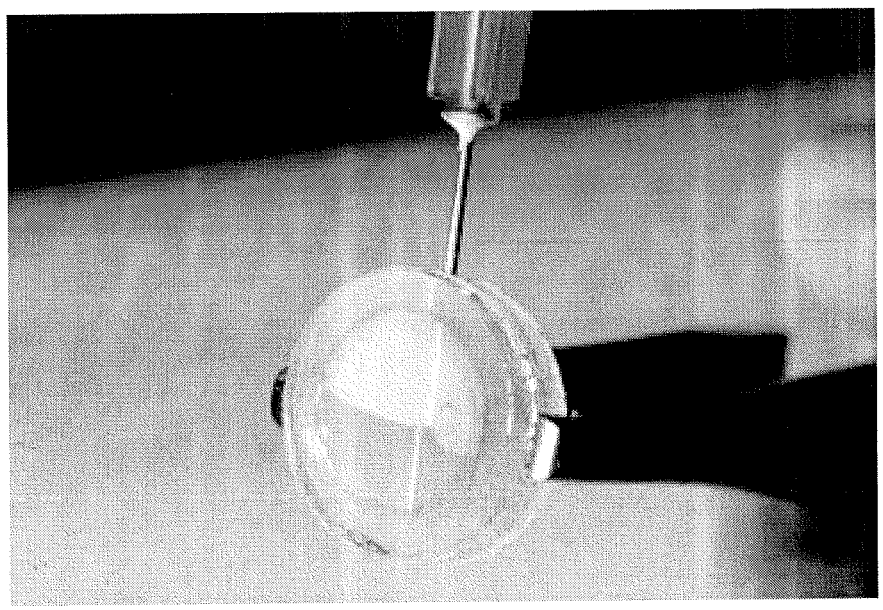
FIGS. 2A and 2B show how the diffusion chambers were injected with *S. stercoralis* L3 and implanted into the mice for the challenge experiments, respectively.

Having previously assessed several vaccine candidates unsuccessfully for this infection, a new approach was taken based on the identification of immunogenic and abundant gene products, using certain bioinformatic tools and expressed sequence tag (EST) databases. This resulted in the discovery of a protein termed *Strongyloides stercoralis* immunoreactive antigen (SSIR) which was sequenced and expressed in baculovirus, *K. lactis, E. coli*, and *P. pastoris*, using a plasmid synthesized from a consensus of sequence information: The SSIR antigen was mixed with the adjuvant alum, and used to immunize mice. In two separate sets of experiments disclosed below, the immunization protocol protected mice (70-90% protection) from challenge infection with *S. stercoralis*. Moreover, sera from protected mice when transferred to naive mice, protected these naive mice from challenge infection.

In an embodiment, the present invention provides an isolated antigen from *S. stercoralis* stage L3, comprising the SSIR protein.

In another embodiment, the invention provides a polynucleotide which encodes the SSIR antigen of *S. stercoralis* and is provided as SEQ ID NO: 1.

In an alternate embodiment the invention provides a polynucleotide which is complementary to the polynucleotide provided as SEQ ID NO: 1.

In another embodiment, the invention provides a SSIR polypeptide having the amino acid sequence of SEQ ID NO: 2, encoded by the polynucleotide of SEQ ID NO: 1.

In another embodiment, the invention provides a composition comprising the polynucleotide of SEQ ID NO: 1, and a pharmaceutically acceptable carrier. It is contemplated, in another embodiment, that the composition further comprise an adjuvant.

In yet another embodiment, the invention provides for a composition comprising the polypeptide of SEQ ID NO: 2, and a pharmaceutically acceptable carrier. It is contemplated, in yet another embodiment, that the composition further comprise an adjuvant.

In an embodiment, the invention also provides a method of use of the polypeptide of SEQ ID NO: 2, to prepare a therapeutic composition or vaccine against *S. stercoralis*.

In a further embodiment, the invention provides a method of vaccinating a patient against *S. stercoralis* infection comprising introducing into the patient, a composition comprising the polypeptide of SEQ ID NO: 2, and a pharmaceutically acceptable carrier under conditions sufficient for said patient to develop a protective immune response.

In yet another embodiment, the invention provides a method of use of the SSIR antigen (SEQ ID NO: 2) encoded by the polynucleotide of SEQ ID NO: 1 for identifying analogous antigens in other parasitic nematodes.

In yet a further embodiment, the invention provides a method of use of the SSIR antigen (SEQ ID NO: 2) encoded by the polynucleotide of SEQ ID NO: 1 for identifying analogous antigens which can act as an immunosuppressant in patients with severe allergies.

In an embodiment, the present invention also provides pharmaceutical composition comprising the SSIR antigen from *S. stercoralis* stage L3, or the SSIR polypeptide of SEQ ID NO: 2 encoded by the polynucleotide of SEQ ID NO: 1, and physiologically acceptable carrier, in an amount effective for use in a medicament, and most preferably for use as a medicament for inducing an immune response in a subject against *S. stercoralis* infection, wherein administration of the medicament to the subject is performed under conditions sufficient for said subject to develop a protective immune response. The pharmaceutical composition can also include, in an embodiment, adjuvants, for example, such as alum, Fruend's complete adjuvant, or various oils, fatty acids, bacterial cell walls, and others known in the art. It is also contemplated that the route of administration of the medicament to the subject can be any physiologically and pharmaceutically acceptable route, including, for example, but not limited to, intranasal, intradermal, subcutaneous, intramuscular or intravenous.

The isolated or purified polypeptides, antigens, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the isolated or purified polypeptides, antigens, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The isolated or purified polypeptides, antigens, and/or proteins of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual, 3$^{rd}$ ed.*, Cold Spring Harbor Press, Cold Spring Harbor, N.Y. 2001; and Ausubel et al., *Current Protocols in Molecular Biology*, Greene Publishing Associates and John Wiley & Sons, NY, 2007. Further, some of the polypeptides, and proteins of the invention (including functional portions and functional variants thereof) can be isolated and/or purified from a source, such as a plant, a bacterium, an insect, a Mammal, e.g., a rat, a mouse, a human, etc. Methods of isolation and purification are well-known in the art. Alternatively, the polypeptides, antigens, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides, and proteins can be synthetic, recombinant, isolated, and/or purified.

Included in the scope of the invention are conjugates, e.g., bioconjugates, comprising any of the inventive polypeptides, antigens, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.*, 298:209-223 (2005) and Kirin et al., *Inorg. Chem.*, 44(15): 5405-5415 (2005)).

By "nucleic acid" as used herein includes "polynucleotide," "oligonucleotide," and "nucleic acid molecule," and generally means an isolated or purified polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethyl guanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudo uracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl)uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The isolated or purified nucleic acids of the invention can be incorporated into a recombinant expression vector. In this regard, an embodiment of the invention provides recombinant expression vectors comprising any of the isolated or purified nucleic acids of the invention. For purposes herein, the term "recombinant expression vector" means a genetically-modified oligonucleotide or polynucleotide construct that permits the expression of an mRNA, protein, polypeptide, antigen or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagem, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is an *E. coli* vector. More preferably, the recombinant expression vector is an bacmid vector, for example, such as *E. coli* DH10 Bac.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, insect or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant mutated vaccine polypeptide, or protein, the host cell is preferably a mammalian cell. Most preferably, the host cell is a human cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

Another embodiment of the invention further provides an antibody, or antigen binding portion thereof, which specifically binds to the SSIR protein antigen or isolated or purified peptide fragments thereof described herein. In one embodiment, the antibody, or antigen binding portion thereof, binds to an epitope or peptide fragment which contains any of the mutant amino acids which differ from the wild-type proteins. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the mutated portion of the SSIR protein or peptide fragments thereof of the present invention, such that there is minimal cross-reaction with other peptides or proteins.

Methods of testing antibodies for the ability to bind to any functional portion of any of the SSIR antigen or isolated or purified peptide fragments thereof are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, Eur. J. Immunol., 5:511-519 (1976), Harlow and Lane (eds.), Antibodies: A Laboratory Manual*, CSH Press (1988), and C. A. Janeway et al. (eds.), *Immunobiology,* $5^{th}$ Ed., Garland Publishing, New York, N.Y. (2001)). Alternatively, other methods, such as EBV-hybridoma methods (Haskard and Archer, *J. Immunol. Methods,* 74(2):361-67 (1984), and Roder et al., *Methods Enzymol.,* 121:140-67 (1986)), and bacteriophage vector expression systems (see, e.g., Huse et al., *Science,* 246:1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al., supra. Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.,* 235:959-973 (1994).

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The vaccine polypeptides, proteins, antigens, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The choice of carrier will be determined in part by the particular vaccine protein, as well as by the particular method used to administer the SSIR protein antigen. Accordingly, there are a variety of suitable formulations of the pharmaceutical composition of the invention. The following formulations for parenteral, subcutaneous, intravenous, intramuscular, intraarterial, intrathecal and interperitoneal administration are exemplary and are in no way limiting. More than one route can be used to administer the vaccine protein, and in certain instances, a particular route can provide a more immediate and more effective response than another route.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the SSIR protein antigen in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the SSIR vaccine protein administered should be sufficient to effect, e.g., a therapeutic or prophylactic response, in the subject over a reasonable time frame. The dose will be determined by the efficacy of the particular SSIR protein and the condition of a human, as well as the body weight of a human to be treated.

The dose of the SSIR antigen based vaccine also will be determined by the existence, nature and extent of any adverse side effects that might accompany the administration of a particular SSIR antigen. Typically, the attending physician will decide the dosage of the SSIR antigen vaccine with which to treat each individual patient, taking into consideration a variety of factors, such as age, body weight, general health, diet, sex, vaccine protein to be administered, route of administration, and the severity of the condition being treated. By way of example and not intending to limit the invention, the dose of the SSIR vaccine can be about 0.001 to about 1000 mg/kg body weight of the subject being treated/day, from about 0.01 to about 10 mg/kg body weight/day, about 0.01 mg to about 1 mg/kg body weight/day.

Alternatively, the SSIR antigen vaccine can be modified into a depot form, such that the manner in which the vaccine protein is released into the body to which it is administered is controlled with respect to time and location within the body (see, for example, U.S. Pat. No. 4,450,150). Depot forms of SSIR proteins can be, for example, an implantable composition comprising the vaccine proteins and a porous or non-porous material, such as a polymer, wherein the SSIR antigen is encapsulated by or diffused throughout the material and/or degradation of the non-porous material. The depot is then implanted into the desired location within the body and the SSIR proteins are released from the implant at a predetermined rate.

With respect to the inventive method of detecting any of the SSIR protein or nucleic acid molecules in a host, the sample of cells of the host can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the host. Preferably, the contacting is in vitro.

In an embodiment, the SSIR vaccine antigen, being proven efficacious in a vaccine against *S. stercoralis*, can be used to identify homologous antigens in other parasitic nematodes. These homologous antigens are then used in vaccines to prevent infection with other nematodes such as hookworms or filarial worms. For example, in an embodiment, the present invention provides a method of identify homologous antigens in other parasitic nematodes comprising obtaining a polynucleotide or polypeptide sequence from a target parasitic nematode or from a database that contains polynucleotide or polypeptide sequences from a target parasitic nematodes, comparing the polynucleotide or polypeptide sequence from a target parasitic nematode with the polynucleotide of SEQ CD NO: 1, or the polypeptide of SEQ ID NO: 2 from *Strongyloides stercoralis*; and determining whether there is sufficient sequence homology (preferably, sequence similarity) between the polynucleotide or polypeptide sequence from the target parasitic nematode and the polynucleotide of SEQ ID NO: 1, or the polypeptide of SEQ ID NO: 2 from *Strongyloides stercoralis*.

Infection with *S. stercoralis* has been shown to reduce the response of mice to allergens. See, Wang, C. C., T. J. Nolan, G. A. Schad, and D. Abraham, *Clin. Experimental Allergy*, 31:495-500 (2001), where it was shown that infection of mice with the helminth *S. stercoralis* suppressed pulmonary allergic responses to ovalbumin. As such, the *S. stercoralis* SSIR antigen can be used to immunize a subject with the objective of reducing allergic responses to allergens.

In an embodiment, the present invention provides a method of suppression allergic activity in a subject comprising administering to a subject the polynucleotide of SEQ ID NO: 1, or the polypeptide of SEQ ID NO: 2, in an amount sufficient to provide an immunosuppressant effect on the allergic activity of the subject.

In another embodiment, the present invention provides a pharmaceutical composition comprising the polynucleotide of SEQ ID NO: 1, or the polypeptide of SEQ ID NO: 2, wherein the composition includes a pharmaceutically and physiologically acceptable carrier, in an amount effective for use in a medicament, and most preferably for use as a medicament to provide an immunosuppressant effect on the allergic activity of a subject, wherein administration of the medicament to the subject is performed under conditions sufficient for said subject to develop an immunosuppressed allergic activity.

EXAMPLES

The following examples further illustrate the invention but, of course, should not be construed as in any way limiting its scope.

Example 1

The following example describes the methods used in the cloning of SsImm-His6 (SSIR-His6).

The vector pDonr253 is a Gateway Donor vector modified from pDonr201 (Invitrogen Corp). The vector pDonr253 replaces the kanamycin resistance gene with a gene encoding spectinomycin resistance, and contains several sequencing primer sites to aid in sequence verification of Entry clones. The pDest-670 vector is a Gateway Destination vector modified from the pFastBac-Dual vector (Invitrogen Corp, Carlsbad, Calif.) which incorporates a GFP reporter gene downstream of the p10 promoter, and a Gateway cassette downstream of the polyhedrin promoter. The following oligonucleotide primers (Operon, Inc., Huntsville, Ala.) were used in isolating the SSIR antigen sequence:

TABLE 1

| | |
|---|---|
| 55162 | 5' CTTCTGGCCGCTGCAGCCCATTCTGCATTTGCGaactccg cccgcgtggagaatc (SEQ ID NO: 3) |
| L5164 | 5' GCTTCTGGCCGCTGCAGCCCATTCTGCATTTGCGaactcc gcccgcgtggagaatc (SEQ ID NO: 4) |
| L4766 | 5' GGGGACAACTTTGTACAAAAAAGTTGGCACCATGGTAAGCG CTATTGTTCTGTACGTGCTTCTGGCCGCTGCAGCCC (SEQ ID NO: 5) |

The SsImm-His6 gene from was cloned by PCR from DNA containing the SSImm (SSIR) sequence (FIG. 1A) using primers corresponding to the 5' and 3' ends of the mature SsImm (SSIR) gene and an adapter-overlap PCR to introduce Gateway recombination sites and a insect cell GP67 signal peptide leader sequence into the gene. To begin, 5 cycles were run using 5 pmol of primers L5162 and L5164, and then 5 pmol of adapter primer L4766 was then added, and the PCR was continued for another 15 cycles. PCR was carried out using Phusion polymerase (New England Biolabs, Ipswich, Mass.) under standard conditions using a 20 second extension time. The final PCR product contained the mature SSImm (SSIR) gene with a GP67 leader sequence at the 5' end preceded by a Gateway attB1 site, and a His6 tag at the carboxy terminal end, followed by a Gateway attB2 site. The PCR product was then cleaned using the QiaQuick PCR purification kit (Qiagen, Germantown, Md.), and recombined into the pDonr253 vector using the Gateway BP recombination reaction (Invitrogen), using the manufacturer's protocols. The subsequent entry clone was sequence verified using internal and external primers to verify the complete insert sequence.

Example 2

The following example details the methods used for subcloning of SsImm-His6 (SSIR-His6).

The sequence-verified entry clone was subcloned by Gateway LR recombination (Invitrogen) into the pDest-670 vector for insect cell expression. Final expression clones were verified by size and restriction digest pattern. The expression clones were then transformed into *E. coli* DH10Bac (Invitrogen), and plated on selective media containing gentamycin, kanamycin, tetracycline, IPTG, and X-gal as per the manufacturer's protocols. White colonies were selected from these plates, and bacmid DNA was generated by alkaline lysis plasmid preparation and verified by PCR amplification across the bacmid junctions.

Example 3

The following example describes the methods used to extract the expression products from the bacmid preparations.

Cell pellets from 2 ml of expression cultures were resuspended in 1 ml of lysis buffer (20 mM HEPES, pH 7.3, 300 mM NaCl, 5% glycerol, 5 mM $MgCl_2$, 2 mM bME, 80 ml of Complete-EDTA protease inhibitor solution (one tablet/ml of $H_2O$), treated with Benzonasc (5 U/ml) and sonicated until cells were >99% lysed as determined by microscopic examination. Soluble and insoluble fractions were separated by centrifugation at 50,000×g for 20 min at 4° C. Soluble and insoluble protein from 30,000 cells (~5-10 microliters) was analyzed by SDS-PAGE.

Example 4

The following example describes the methods used for SDS-PAGE analysis of the expressed proteins.

All gel samples were prepared using LDS sample buffer (Invitrogen, 141 mM Tris base, 2% LDS, 10% Glycerol, 0.51 mM EDTA, 0.22 mM SERVA® Blue G250, 0.175 mM Phenol. Red, pH 8.5) and 25 mM tris(2-carboxyethyl)phosphine (TCEP) reducing agent (BioRad, Hercules, Calif.). Samples were then heated at 95° C. for 5 minutes before application to Criterion Tris-glycine 10.5%-14% pre-cast gels (BioRad). Electrophoresis was performed at a constant voltage of 200V for 55 min in 1× running buffer (25 mM Tris, pH 8.6, 0.192 mM glycine, 0.1% SDS). Proteins were visualized using 0.005% Coomassie Brilliant Blue R-250 in 0.3% v/v acetic acid, and gel images captured with a Fuji LAS-3000 imaging system. Where applicable, equal percentages of starting, insoluble, load (i.e. soluble) and flow through fractions analyzed. Additionally, equal volumes of equal volume elution fractions were also analyzed.

Example 5

The following example describes the methods used for western blot analysis of the expressed proteins.

After separation by SDS-PAGE, the proteins were transferred to a nitrocellulose membrane using a semi-dry transfer apparatus, (iBlot, Invitrogen) as per the manufacturer's instructions. Antigen was detected using the anti-6×His-HRP (R&D Systems, Minneapolis, Minn.) antibody, at 1:5000 dilution incubated with the membrane overnight at 4° C. in 1×TTBS+3% non-fat dry milk. After washing 5×5 minutes with 1×TTBS, signal was detected with West Pico chemiluminescent detection reagent (Pierce, Rockford, Ill.) and visualized using a Fuji LAS-3000 imaging system (Fujifilm North America, Edison, N.J.).

Example 6

The following example details the care and feeding of the experimental animals.

Male BALB/cByJ mice, six to eight weeks old, were obtained from Jackson Laboratory (Bar Harbor, Me.). Animals were housed in Micro-Isolator boxes (Lab Products Inc., Maywood, N.J.) and were fed autoclaveable Laboratory Rodent Chow (Ralston Purina, St. Louis, Mo.), and sterilized acid water (pH 2.7) ad libitum. The animal housing room was temperature, humidity, and light cycle controlled.

Example 7

The following example describes the preparation of diffusion chambers and their use in challenge infections.

S. stercoralis larvae, stage L3 (L3), were cultured from the fresh stools of infected laboratory dogs. L3 were harvested from charcoal cultures and washed via centrifugation and resuspension in sterile 1:1 NCTC-135 and IMDM medium supplemented with 100 U/ml penicillin, 0.1 mg/rill streptomycin, 0.1 mg/ml gentamicin (Sigma Chemical Co., St. Louis, Mo.) and 0.25 mg/ml levaquin. (Ortho-McNeil, Raritan, N.J.).

Figure 2B:
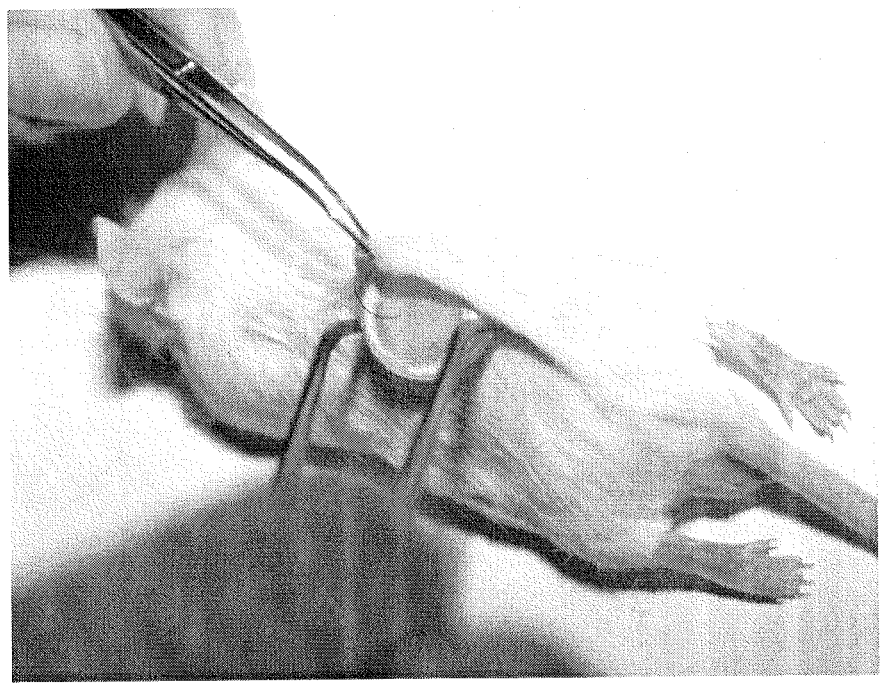

Diffusion chambers were constructed from 14 mm Lucite rings (Millipore, Bedford, Mass.), covered with 2.0 µm pore membranes (Millipore, Bedford, Mass.) using cyanoacrylate adhesive (Superglue Corp., Hollis, N.Y.), fused together with an adhesive consisting of 1:1 1,2-dichloroethane (Fisher Scientific, Pittsburgh, Pa.) acryloid resin (Rohm and Haas, Philadelphia, Pa.) and then sterilized via 100% ethylene oxide. Fifty L3 were injected into the diffusion chambers that were then surgically implanted in a subcutaneous pocket created on the flank of the mice (FIGS. 2A-2B). At the conclusion of the experimental time period, larval viability was determined based on motility and morphology, and both sera and diffusion chamber fluids were recovered for further analysis.

Example 8

The following example describes the immunization and challenge protocols used in the experiments.

Figure 3A:
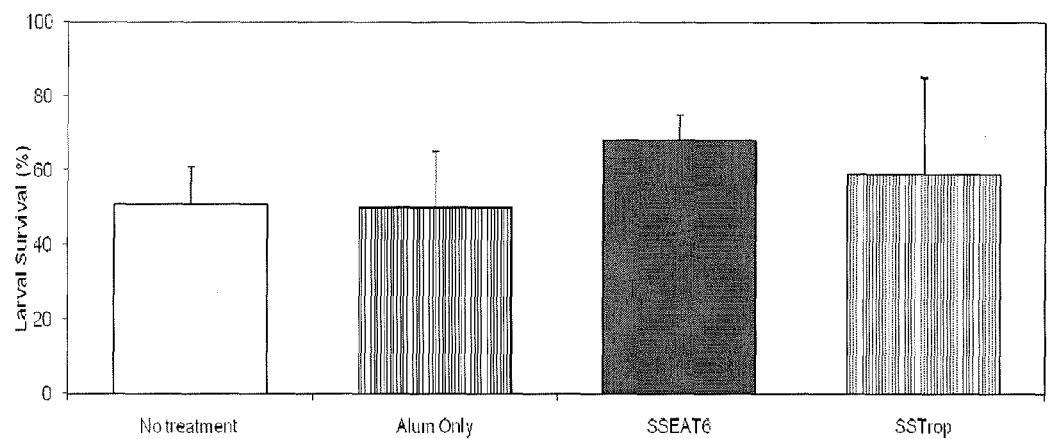
FIGS. 3A and 3B depict two graphs where mice were challenged with different *S. stercoralis* antigens and where the percentage of nematode larval survival was measured after exposure.
Figure 3B:
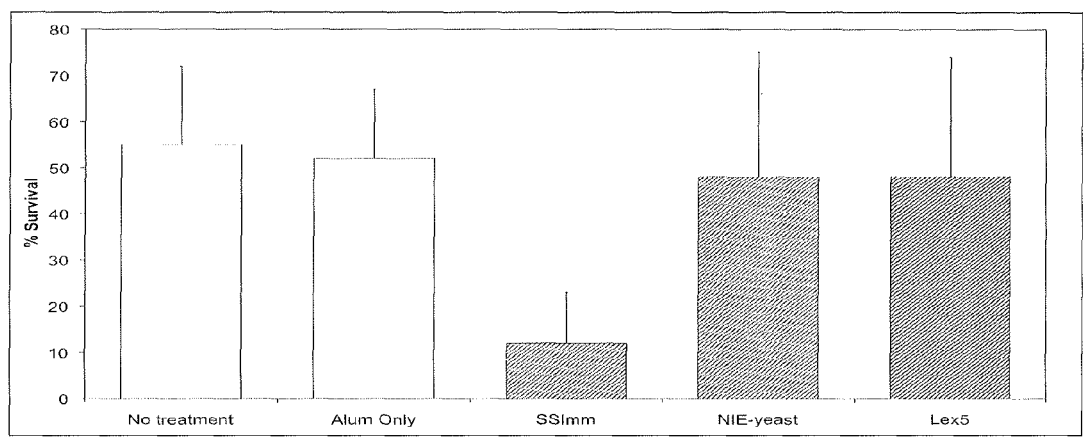
Figure 4:
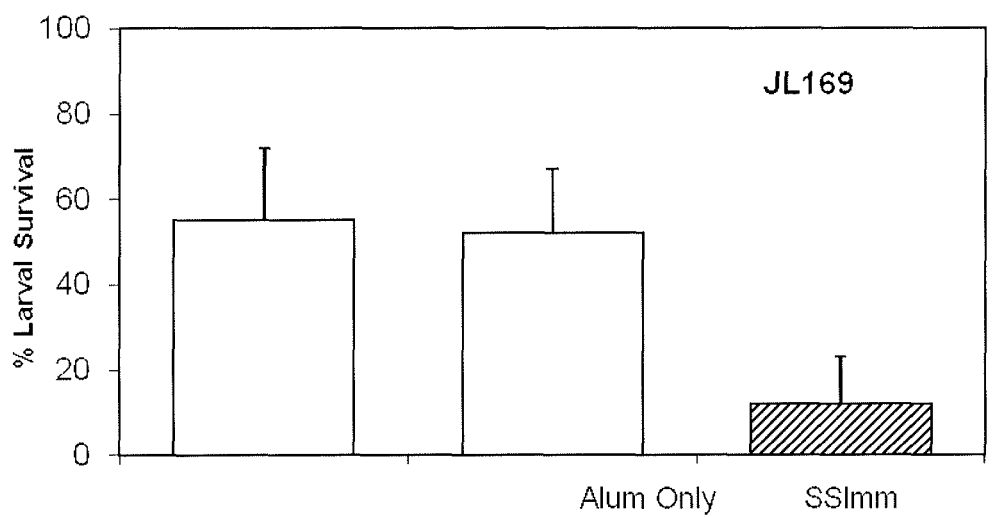
FIG. 4 shows the results of challenge experiment JL169, showing that the immune response generated to the antigen SSImm (SSIR) was effective in killing *S. stercoralis* larvae.
Figure 5:
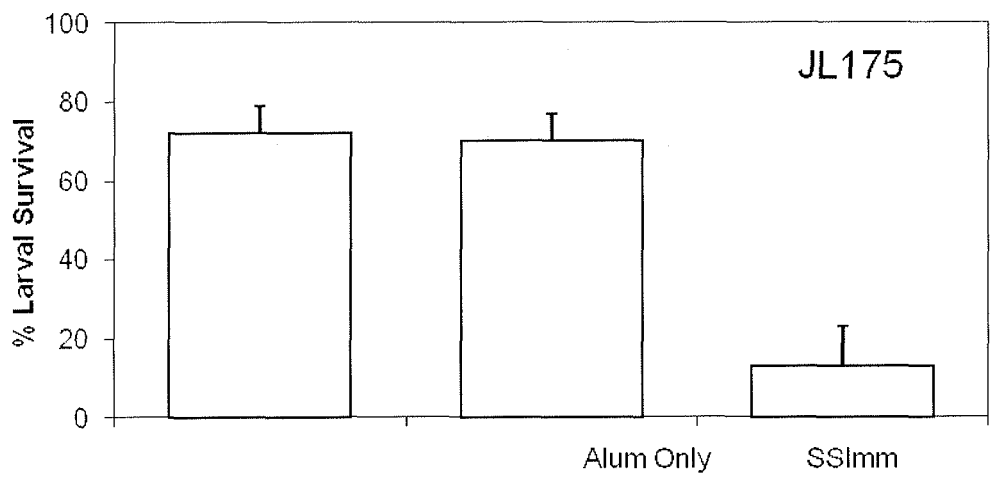
FIG. 5 shows the results of challenge experiment JL175, showing that the immune response generated to the antigen SSImm (SSIR) was effective in killing *S. stercoralis* larvae.

Mice were immunized with 25 µg of each recombinant antigen in 0.1 ml of PBS, injected subcutaneously into the nape of the neck with 0.1 ml of low viscosity alum 2 mg/ml in PBS (Reheis Inc., Berkeley Heights, N.J.). A booster immunization followed 14 days later with the same quantity of antigen in with alum or control. On day 28, mice received a challenge infection within a diffusion chamber and the diffusion chambers were recovered from the mice 4 days after implantation. At the time of diffusion chamber recovery, mice were anesthetized with methoxyflurane (Pitman-Moore, Inc., Mundelein, Ill.) and then killed by exsanguination. Serum was then prepared for subsequent antibody analyses. Diffusion chamber contents were analyzed to assess larval survival and the nature of the cellular infiltration into the diffusion chamber. Larvae recovered from diffusion chambers were considered live if they exhibited motility (FIGS. 3A-3B). Cells found within the diffusion chambers were collected by centrifugation onto slides using a Cytospin 3 (Shandon Inc., Pittsburgh, Pa.) and then stained for differential counts with DiffQuik (Baxter Healthcare Corp., Miami, Fla.).

Example 9

The following example describes the use of ELISA assays to quantify antibodies generated to the SSIR antigen.

Figure 6:
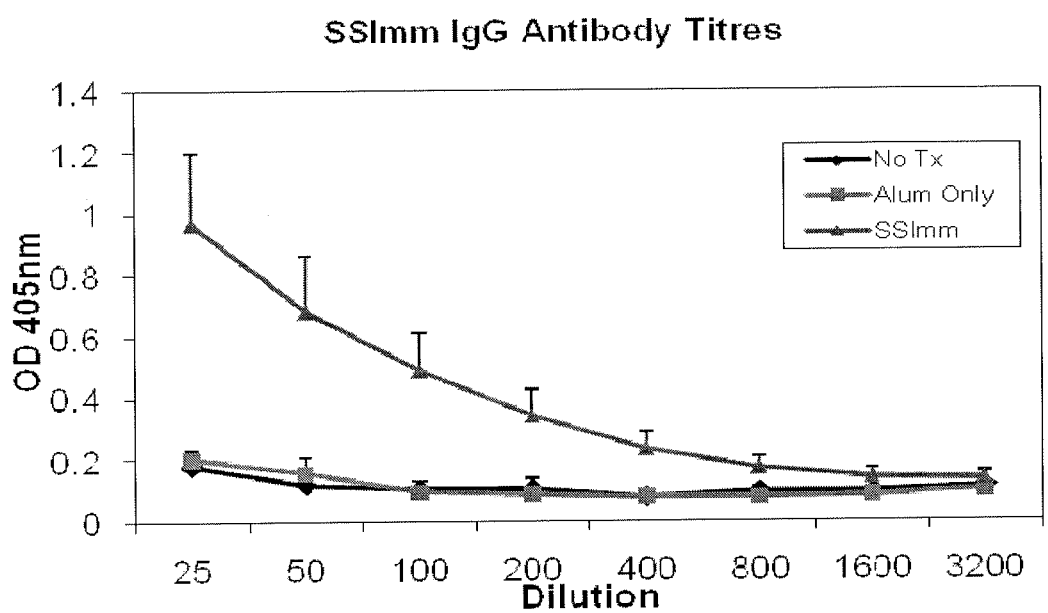
FIG. 6 is a graph depicting the levels of antibody titer to the *S. stercoralis* antigen SSImm (SSIR) in the mice of experiment JL169.
Figure 7:
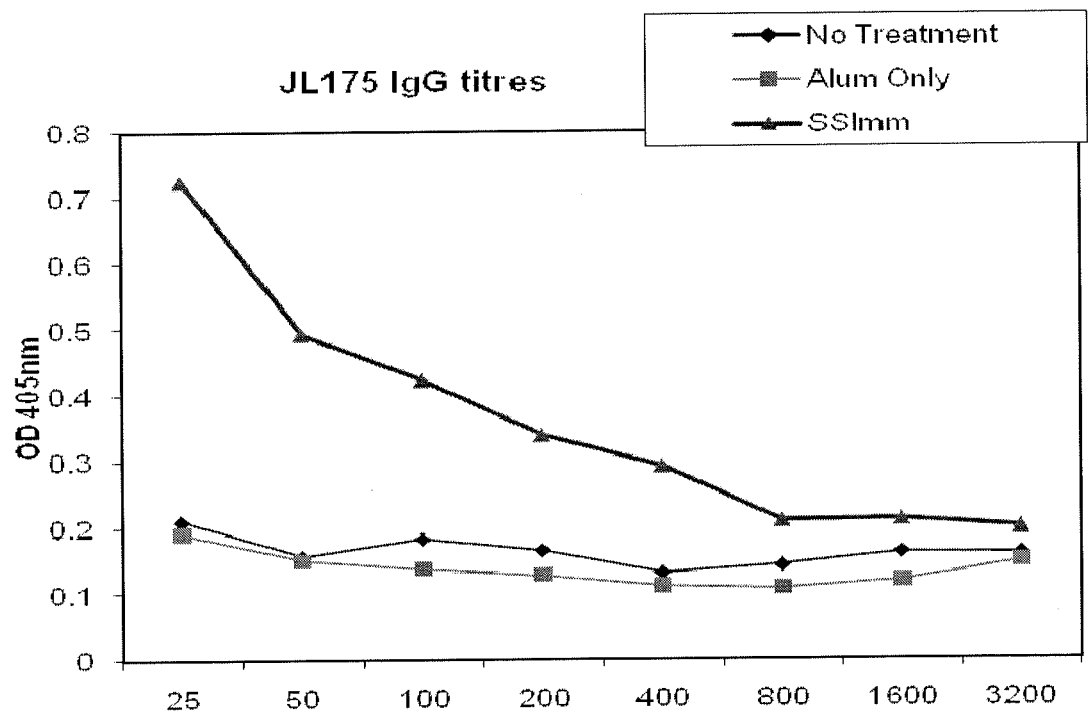
FIG. 7 is a graph depicting the levels of antibody titer to the antigen SSImm (SSIR) in the mice of experiment JL175.

Serum levels of antigen-specific IgG antibodies were measured by ELISA. Fifty of a solution containing 2 µg/ml of recombinant antigen in 50 mM Tris-Cl pH 8.8, was placed in the wells of 96 well Maxisorp plates (Nalge Nunc International, Rochester, N.Y.) overnight. After washing, 200 µl/well of blocking buffer (0.17 M Boric Acid, 0.12 M NaCl, 1 mM EDTA, 0.25% BSA, 0.05% Tween 20, pH 8.5) (BBS) was added to each well. Individual sera were diluted in BBS, followed by biotinylated anti-mouse IgG (Pharmingen, San Diego Calif.) diluted 1:250. Extravidin peroxidase diluted 1:1000 (Sigma, St. Louis) was added to the wells followed by ABTS (one component, KPL, Gaithersburg, Md.). Optical densities were read at 405 nm in a Bio-Rad 3550 Microplate reader (Bio-Rad, Hercules, Calif.) after overnight incubation (FIGS. 6-7).

Example 10

The following example illustrates the ability of serum from immunized mice to confer protection from S. stercoralis infection.

Figure 8:
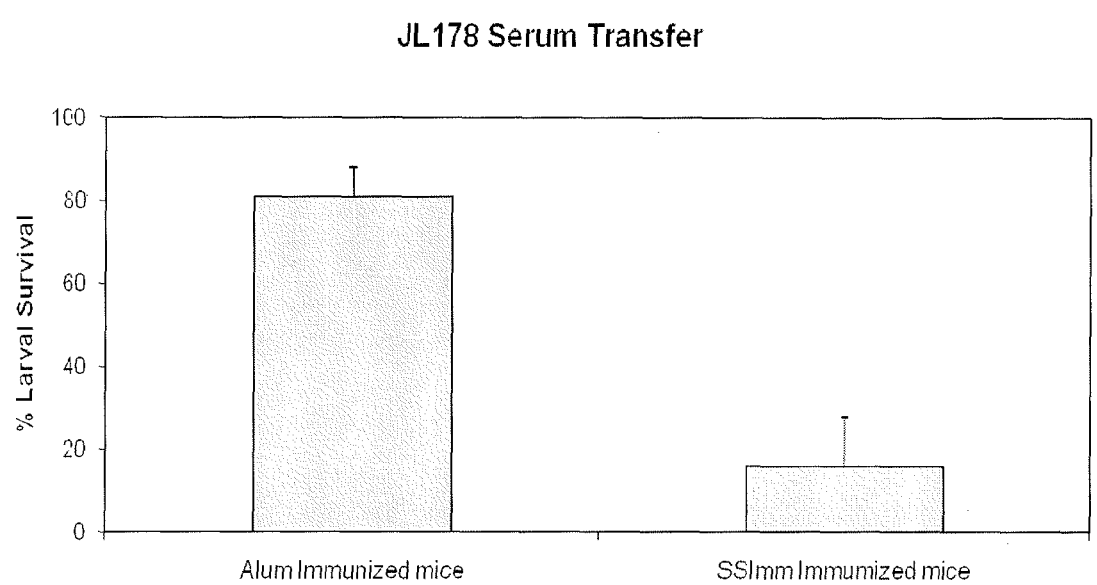
FIG. 8 is a graph depicting the percentage of *S. stercoralis* larvae alive implanted in naïve mice, after the mice were administered serum from mice previously challenged with the antigen SSImm (SSIR) or adjuvant alone.

Serum recovered from mice immunized with either the SSIR antigen, or adjuvant alone (control), as described in Example 7, was collected at the time that the diffusion chambers were recovered. The serum from immunized mice was passed through a Gammabind Plus protein G Sepharose column (Amersham Pharmacia Biotech AB, Uppsala, Sweden) to separate IgM, IgA, and IgE, which flowed through the column, from the IgG, which bound to the beads. The IgG fraction was eluted from the column using 0.5 M acetic acid, pH 3.0, which was immediately neutralized with saturated Tris-HCl, pH 9.8. The IgM, IgA, and IgE fractions were further separated by sequential passage through anti-mouse IgE and anti-mouse IgA affinity columns prepared as previously described (Brigandi et al., 1996). One hundred microliters of serum from control and immunized mice was diluted to 200 µl with PBS, and then transferred into the subcutaneous pocket, in which a diffusion chamber was inserted for 24 hours. An enzyme-linked immunosorbent assay (ELISA) determined the quantity of each isotype found in 100 µl of serum. This quantity of antibody was diluted into 200 µl of PBS and injected into naïve mice as described above in Example 7 (FIG. 8).

Statistical Analyses. Data were analyzed by MGLH multifactorial ANOVA in Systat 5.2 (Systat, Inc., Evanston, Ill.). Probability values of less than 0.05 were considered significant.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising an isolated antigen from *Strongyloides stercoralis* stage L3, the antigen comprising *Strongyloides stercoralis* immunoreactive antigen (SSIR) protein, an adjuvant, and a pharmaceutically acceptable carrier, wherein the SSIR antigen comprises SEQ ID NO: 2 or is encoded by the nucleotide sequence comprising SEQ ID NO: 1.

2. A vaccine effective for protecting a mammal against *Strongyloides stercoralis* infection, the vaccine comprising an effective amount of an isolated antigen from *Strongyloides stercoralis* stage L3, an adjuvant, and a pharmaceutically acceptable carrier, wherein the antigen comprises *Strongyloides stercoralis* immunoreactive antigen (SSIR) protein, wherein the antigen comprises SEQ ID NO: 2 or is encoded by the nucleotide sequence comprising SEQ ID NO: 1.

3. The pharmaceutical composition of claim 1, wherein the adjuvant is alum.

4. A method of inducing an immune response against *Strongyloides stercoralis* in a mammal, the method comprising administering the pharmaceutical composition of claim 1 to the mammal in an amount effective to induce an immune response against *Strongyloides stercoralis* in the mammal, wherein the immune response is effective in killing *Strongyloides stercoralis* larvae and protecting the mammal against *Strongyloides stercoralis* infection and wherein the amount administered is 0.001 to 1000 mg/kg body weight of the mammal per day.

5. The method of claim 4, wherein the mammal is a human.

6. The method of claim 4, comprising administering the SSIR antigen intranasally, intradermally, subcutaneously, intramuscularly or intravenously.

7. The vaccine of claim 2, wherein the adjuvant is alum.

8. The method of claim 4, wherein the method provides 70-90% protection from challenge infection with *Strongyloides stercoralis*.

9. The method of claim 4, wherein the method increases the anti-*Strongyloides stercoralis* antibody titer in the mammal as compared to the anti-*Strongyloides stercoralis* antibody titer in an untreated mammal.

10. The method of claim 4, wherein the adjuvant is alum.

11. The method of claim 8, wherein the adjuvant is alum.

12. The method of claim 9, wherein the adjuvant is alum.

13. The method of claim 4, wherein the amount administered is 0.01 to 10 mg/kg body weight of the mammal per day.

14. The method of claim 4, wherein the amount administered is 0.01 mg to 1 mg/kg body weight of the mammal per day.

* * * * *